(12) United States Patent
Weisgerber et al.

(10) Patent No.: US 6,410,017 B1
(45) Date of Patent: *Jun. 25, 2002

(54) PERSONAL CARE COMPOSITIONS CONTAINING ACTIVE PROTEINS TETHERED TO A WATER INSOLUBLE SUBSTRATE

(75) Inventors: David John Weisgerber; Andrew Campbell Allcock, both of Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/401,093

(22) Filed: Sep. 22, 1999

Related U.S. Application Data

(60) Provisional application No. 60/101,361, filed on Sep. 22, 1998.

(51) Int. Cl.[7] .............................................. A61K 38/43
(52) U.S. Cl. ................. 424/94.1; 424/94.63; 424/94.6; 424/94.3; 424/443
(58) Field of Search ............................ 424/94.63, 94.6, 424/94.1, 94.3, 443

(56) References Cited

U.S. PATENT DOCUMENTS

| | | | |
|---|---|---|---|
| 4,179,337 A | 12/1979 | Davis et al. | ................. 435/181 |
| 4,556,554 A | 12/1985 | Calvo | ........................... 424/70 |
| 5,446,090 A | 8/1995 | Harris | ....................... 525/54.1 |
| 5,554,508 A | 9/1996 | Auriol et al. | ............... 435/68.1 |
| 5,691,060 A | 11/1997 | Levy | ...................... 428/402.21 |

FOREIGN PATENT DOCUMENTS

| | | | |
|---|---|---|---|
| CA | 1229808 | 12/1987 | ........... C08B/11/20 |
| FR | 2676451 A1 | 11/1992 | ........... C08F/12/08 |
| GB | 2240040 A | 7/1991 | ........... C12N/11/02 |
| JP | 59-011183 | 1/1984 | ........... C12N/11/04 |
| JP | 60-237993 A | 11/1985 | ........... C12N/11/12 |
| JP | 07-126151 | 5/1995 | ............ A61K/7/50 |
| WO | WO 95/15352 | 6/1995 | ............ C08H/1/00 |
| WO | WO 96/21469 | 7/1996 | .......... A61K/47/48 |

OTHER PUBLICATIONS

Cho, M.Y. & Einolf, D.M., "Application of Immobilized Cells and Enzymes for Pharmaceutical Production", *Pharmaceutical Manufacturing,* 1985 (Oct.), 39–42.

Huang, W., et al., "Improving the Activity of Immobilized Subtilisin by Site–specific Attachment to Surfaces", *Analytical Chemistry,* 1997 (Nov.), vol. 69 (No. 22), 4601–4607.

Plate, N.A., et al., "Multi–functional Biologically–active Systems Modified with Synthetic Polymers", *STP Pharma Sciences,* 1994, 4(5), 313–323.

*Primary Examiner*—Jean C. Witz
(74) *Attorney, Agent, or Firm*—Marianne Dressman; Tara M. Rosnell; Stephen W. Miller

(57) ABSTRACT

The present invention relates to personal care compositions comprising a water insoluble substrate, a plurality of active proteins, and a binding means, comprising a polymeric tether, permanently attaching each of the enzymes to the substrate wherein the personal care composition comprises from about 0.01 $\mu g/cm^2$ to about 1000 $\mu g/cm^2$ of the enzyme on the substrate.

44 Claims, No Drawings

PERSONAL CARE COMPOSITIONS CONTAINING ACTIVE PROTEINS TETHERED TO A WATER INSOLUBLE SUBSTRATE

This application claims the benefit of provisional application No. 60/101,361, field Sep. 22, 1998.

TECHNICAL FIELD

The present invention relates to personal care compositions comprising active proteins bound to a water insoluble substrate via a polymeric tether. Embodiments of the personal care compositions include a personal care wipe and a personal care skin mask. The compositions herein provide improved cleansing and skin conditioning due to the activity of the active proteins, with minimized risk of allergic reaction to the active protein by the user.

BACKGROUND OF THE INVENTION

An increasing number of commercial products containing active proteins are becoming available. The majority of these products utilize an enzyme, as the active protein. Enzymes are proteins which react with a compound, or substrate, to break down that compound. Enzymes are divided into numerous classes based on the class of substrate they react upon. Each class of enzyme generally catalyzes the severing of different chemical bonds resulting in the specific selection of activity. The lipase class of enzymes are known for their ability to hydrolyze ester bonds created between, but not limited to, hydrocarbons and polyalcohol backbone substrates. Examples of these substrates are mono-, di-, and triglyceride polyglycerol esters. The protease class of enzymes are known for their ability to hydrolyze proteins. Naturally occurring and bio-engineered protease enzymes are incorporated into household cleaning detergents to hydrolyze proteinaceous dirt and stains, into personal care products to remove dirt and dead skin, into oral cleansing products to facilitate plaque removal in the mouth, and into medicines to affect undesired proteins in the body.

It is known that current commercial cleansing products are made more effective by the incorporation of protease enzymes. U.S. Pat. No. 4,261,868 (Hora et al.), U.S. Pat. No. 4,404,115 (Tai), U.S. Pat. No. 4,318,818 (Letton et al.), European Patent Application 130,756 (published Jan. 9, 1985) and U.S. Pat. No. 5,030,378 (Venegas) all disclose the use of protease enzymes in cleansing or detergent products.

It is also realized, however, that many active proteins, including enzymes, are potential antigens, and may cause allergic reactions in humans under certain conditions. The human immune system can produce specific antibodies upon exposure to active proteins. This process of producing specific antibodies is referred to as "immunization" when a clinically beneficial response is obtained. When the response leads to hypersensitivity, however, it is referred to as "sensitization". Allergenic sensitization to active proteins has been observed in environments where humans are regularly exposed to the protein. Such environments include manufacturing facilities, where workers can be exposed to uncontrolled dust or aerosol containing an active protein, or the marketplace, where consumers' repeated use of products containing active proteins has, on occasion, caused an allergic reaction.

Presently, allergic responses to active proteins can be minimized by limiting the selection of those proteins used in products to those of human origin. While this approach minimizes allergenicity problems, it is not a complete solution since it is often not possible to find such an active protein which also has the activity properties desired.

Another way of diminishing allergic response has been to reduce the size of the protein molecules (see JP Patent Publication Number 4,112,753). However, size reduction may also cause a significant reduction in biological activity.

A third proposition for decreasing allergenicity is through epitope mapping and alteration of the protein amino acid sequence to deliver a protein with reduced allergenicity. This approach usually requires a large investment of development time and money.

In the medical field, suggestions have been made to diminish the immunogenicity of proteins through yet another method. This method involves attaching unreactive polymers to the protein. U.S. Pat. No. 4,179,337 (Davis, et al.) relates to enzymes coupled to substantially straight chain polyethylene glycol (PEG) or polypropylene glycol (PPG) polymer moieties. While PEG/PPG coupling was found to mitigate the allergenicity of the enzyme, only 15% of the physiological activity was maintained. PCT Application WO 96/17929 (Olsen, et al., published Jun. 13, 1996) relates to the modification of enzymes by conjugating them with suitable polymers. The Olsen application describes modified enzymes which demonstrate a reduction in allergenicity of from 25% to 66% compared to the parent enzyme, while maintaining from 39% to 100% of the activity of the parent.

The U.S. patent application, Ser. No. 08/903,298 discloses the use of enzymes modified by the addition of twin polyethylene glycol polymer moieties to reduce allergenicity while delivering high enzymatic activity. The modified enzyme therein is used in combination with a fibrous substrate in a wipe application. The modified enzymes are not attached to the substrate. Reduced allergenicity is achieved via the modification of the enzyme.

The U.S. patent application, Ser. No. 09/088,912 disclosed polymeric chemical modification of *subtilisin* enzymes at one or more of three specific epitope regions which were found to mask the immunogenic determinants of the enzyme.

Another approach to reduce the allergenicity of active proteins has been by granulating, coating or dissolving the active proteins to avoid their becoming airborne. U.S. Pat. No. 4,556,554 (Calvo) discloses cosmetic compositions which comprise enzymes which have been immobilized by attachment to particles of polymeric support. The particles with attached enzymes are dispersed in the cosmetic vehicle. Upon application of the vehicle to the skin, the enzyme is released from the support and is therefore reactivated. Methods such as this address consumer exposure to airborne proteins, however they still leave the substantial risks associated with extended tissue contact with the released enzyme which are deposited on the skin.

Canadian Patent 1,229,808, issued Dec. 1, 1987 teach the immobilization of enzymes, specifically β-galactosidase and β-glucosidase, on cellulosic substrates wherein the enzyme is immobilized by absorption into a agarose gel coating the substrate.

UK Patent Application GB 2,240,040, published Jul. 24, 1991 also teaches immobilized enzymes on substrates. Enzymes, therein as covalently bonded to substrates to provide a medicated dressing.

The activity of enzymes used in biological equipment such as biosensors, bioseparators, and bioreactors has been enhanced by the use of site-specific attachment of enzymes to equipment surfaces. See Huang et al., "Improving the Activity of Immobilized *Subtilisin* by Site-specific Attachment to Surface", *Analytical Chemistry*, 69(22), Nov. 15, 1997. Huang teaches the immobilization of *subtilisin* enzymes via mutation of serine 249 or serine 145 to cysteine, and bonding to silica beads functionalized with amino groups.

It would be highly desirable to develop a composition which would provide improved levels of protein activity while maintaining low allergenic responses from exposure to the active proteins. If this were accomplished it would provide consumers with safer ways to utilize the benefits of protein technology.

It is an object of the present invention to provide a personal care composition which delivers this activity while maintaining reduced stimulation of and resulting activation of the immune system. It is also an object of the present invention to provide this biological activity, with reduced risk of allergic reaction in the form of a personal care wipe or a personal care skin mask.

SUMMARY OF THE INVENTION

The present invention relates to personal care compositions comprising a water insoluble substrate, a plurality of active proteins, and a binding means, comprising a polymeric tether, permanently attaching each of the proteins to the substrate wherein the personal care composition comprises from about 0.01 $\mu g/cm^2$ to about 1000 $\mu g/cm^2$ of the protein on the substrate.

DETAILED DESCRIPTION OF THE INVENTION

The personal care compositions of the present invention comprise active proteins permanently bound to a water insoluble substrate with a polymeric tether. The compositions are highly efficacious for cleaning sweat, sebum, dead skin cells, fats and oils from the skin and for moisturizing of the skin. The compositions provide a convenient means to utilize the specialized activity of enzymes and other active proteins. The active proteins are bound to the substrate, thereby minimizing any risk of allergic reaction. By attaching the active proteins to the substrate by way of a polymeric tether the active proteins are more mobile on the surface of the substrate, thereby allowing the proteins easier access to dirt and dead skin cells.

Without being limited by theory, it is believed that by permanently binding the active protein to the substrate, the plurality of proteins may be brought into contact with the skin for use, allowing them to act on the surface. Then as the wipe is removed all of the proteins are lifted from the skin surface, and removed and disposed of with the used wipe, thereby eliminating the risk of aerosolization and extended dermal exposure. The active protein reacts with the compounds it has specific reactivity for while in contact with the skin and none remain on the skin after use to stimulate the immune system and subsequently form antibodies responsible for allergic reaction.

As used herein, the phrase "amino acid sequence" refers to a specific configuration of the amino acids comprising a protein. The following is a list of abbreviations used herein to describe amino acids:

| Amino Acid | Three-letter Abbreviation | One-letter Symbol |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| No amino acid at position | Xaa | * |

As used herein, the term "mutation" refers to the genetic alteration of an organism, which in turn alters the amino acid sequence of the enzyme produced by that organism. The mutation of an organism has been often found to alter the properties of the enzyme.

As used herein, the term "wild-type" refers to an enzyme produced by unmutated hosts.

As used herein, the term "variant", means an enzyme having an amino acid sequence which differs from that of the wild-type enzyme due to the genetic mutation of the host producing that enzyme.

All percentages and ratios used herein, unless otherwise indicated, are by weight and all measurements made are at 25° C., unless otherwise designated. The invention hereof can comprise, consist of, or consist essentially of, the essential as well as optional ingredients and components described therein.

The essential components of the personal care compositions of the present invention, as well as a non-exclusive list of preferred and optional ingredients, are described in detail below.

Water Insoluble Substrate

The products of the present invention comprise a water insoluble substrate. By "water insoluble" is meant that the substrate does not dissolve in or readily break apart upon immersion in water. The water insoluble substrate is the implement or vehicle for delivering the active proteins of the present invention to the skin to be cleansed and moisturized, and for removing substantially all of the proteins from the skin.

A wide variety of materials can be used as the substrate. The following nonlimiting characteristics are desirable: (i) sufficient wet strength for use, (ii) sufficient abrasivity, (iii) sufficient loft and porosity, (iv) sufficient thickness, and (v) appropriate size.

Nonlimiting examples of suitable insoluble substrates which meet the above criteria include nonwoven substrates, woven substrates, hydroentangled substrates, air entangled substrates, natural sponges, synthetic sponges, polymeric netted meshes, and the like. Preferred embodiments employ nonwoven substrates since they are economical and readily available in a variety of materials. By nonwoven is meant that the layer is comprised of fibers which are not woven into a fabric but rather are formed into a sheet, mat, or pad layer. The fibers can either be random (i.e., randomly aligned) or they can be carded (i.e. combed to be oriented in primarily one direction). Furthermore, the nonwoven substrate can be composed of a combination of layers of random and carded fibers.

Nonwoven substrates may be comprised of a variety of materials both natural and synthetic. By natural is meant that the materials are derived from plants, animals, insects or byproducts of plants, animals, and insects. By synthetic is meant that the materials are obtained primarily from various man-made materials or from natural materials which have been further altered. The conventional base starting material is usually a fibrous web comprising any of the common synthetic or natural textile-length fibers, or mixtures thereof.

Nonlimiting examples of natural materials useful in the present invention are silk fibers, keratin fibers and cellulosic fibers. Nonlimiting examples of keratin fibers include those selected from the group consisting of wool fibers, camel hair fibers, and the like. Nonlimiting examples of cellulosic fibers include those selected from the group consisting of wood pulp fibers, cotton fibers, hemp fibers, jute fibers, flax fibers, and mixtures thereof.

Nonlimiting examples of synthetic materials useful in the present invention include those selected from the group consisting of acetate fibers, acrylic fibers, cellulose ester fibers, modacrylic fibers, polyamide fibers, polyester fibers, polyolefin fibers, polyvinyl alcohol fibers, rayon fibers, polyurethane foam, and mixtures thereof. Examples of some of these synthetic materials include acrylics such as acrilan, creslan, and the acrylonitrile-based fiber, orlon; cellulose ester fibers such as cellulose acetate, arnel, and acele; polyamides such as nylons (e.g., nylon 6, nylon 66, nylon 610, and the like); polyesters such as fortrel, kodel, and the polyethylene terephthalate fiber, dacron; polyolefins such as polypropylene, polyethylene; polyvinyl acetate fibers; polyurethane foams and mixtures thereof. These and other suitable fibers and the nonwoven materials prepared therefrom are generally described in Riedel, "Nonwoven Bonding Methods and Materials," *Nonwoven World* (1987); *The Encyclopedia Americana*, vol. 11, pp. 147–153, and vol. 26, pp. 566–581 (1984); U.S. Pat. No. 4,891,227, to Thaman et al., issued Jan. 2, 1990; and U.S. Pat. No. 4,891,228 which are all incorporated by reference herein in their entirety.

Nonwoven substrates made from natural materials consist of webs or sheets most commonly formed on a fine wire screen from a liquid suspension of the fibers. See C. A. Hampel et al., *The Encyclopedia of Chemistry*, third edition, 1973, pp. 793–795 (1973); *The Encyclopedia Americana*, vol. 21, pp. 376–383 (1984); and G. A. Smook, *Handbook of Pulp and Paper Technologies*, Technical Association for the Pulp and Paper Industry (1986); which are incorporated by reference herein in their entirety.

Substrates made from natural materials useful in the present invention can be obtained from a wide variety of commercial sources. Nonlimiting examples of suitable commercially available paper layers useful herein include Airtex®, an embossed airlaid cellulosic layer having a base weight of about 71 gsy, available from James River, Green Bay, Wis.; and Walkisoft®, an embossed airlaid cellulosic having a base weight of about 75 gsy, available from Walkisoft U.S.A., Mount Holly, N.C.

Methods of making nonwoven substrates are well known in the art. Generally, these nonwoven substrates can be made by air-laying, water-laying, meltblowing, coforming, spunbonding, or carding processes in which the fibers or filaments are first cut to desired lengths from long strands, passed into a water or air stream, and then deposited onto a screen through which the fiber-laden air or water is passed. The resulting layer, regardless of its method of production or composition, is then subjected to at least one of several types of bonding operations to anchor the individual fibers together to form a self-sustaining web. In the present invention the nonwoven layer can be prepared by a variety of processes including hydroentanglement, thermally bonding or thermo-bonding, and combinations of these processes. Moreover, the substrates of the present invention can consist of a single layer or multiple layers. In addition, a multilayered substrate can include films and other nonfibrous materials.

Nonwoven substrates made from synthetic materials useful in the present invention can also be obtained from a wide variety of commercial sources. Nonlimiting examples of suitable nonwoven layer materials useful herein include HEF 40-047, an apertured hydroentangled material containing about 50% rayon and 50% polyester, and having a basis weight of about 43 grams per square yard (gsy), available from Veratec, Inc., Walpole, Mass.; HEF 140–102, an apertured hydroentangled material containing about 50% rayon and 50% polyester, and having a basis weight of about 56 gsy, available from Veratec, Inc., Walpole, Mass.; Novonet® 149 -616, a thermo-bonded grid patterned material containing about 100% polypropylene, and having a basis weight of about 50 gsy, available from Veratec, Inc., Walpole, Mass.; Novonet® 149-801, a thermo-bonded grid patterned material containing about 69% rayon, about 25% polypropylene, and about 6% cotton, and having a basis weight of about 75 gsy, available from Veratec, Inc. Walpole, Mass.; Novonet® 149-191, a thermo-bonded grid patterned material containing about 69% rayon, about 25% polypropylene, and about 6% cotton, and having a basis weight of about 100 gsy, available from Veratec, Inc. Walpole, Mass.; HEF Nubtex® 149-801, a nubbed, apertured hydroentangled material, containing about 100% polyester, and having a basis weight of about 70 gsy, available from Veratec, Inc. Walpole, Mass.; Keybak® 95V, a dry formed apertured material, containing about 75% rayon, about 25% acrylic fibers, and having a basis weight of about 43 gsy, available from Chicopee, New Brunswick, N.J.; Keybak® 1368, an apertured material, containing about 75% rayon, about 25% polyester, and having a basis weight of about 39 gsy, available from Chicopee, New Brunswick, N.J.; Duralace® 1236, an apertured, hydroentangled material, containing about 100% rayon, and having a basis weight from about 40 gsy to about 115 gsy, available from Chicopee, New Brunswick, N.J.; Duralace® 5904, an apertured, hydroentangled material, containing about 100% polyester, and having a basis weight from about 40 gsy to about 115 gsy, available from Chicopee, New Brunswick, N.J.; Sontaro 8868, a hydroentangled material, containing about 50% cellulose and about 50% polyester, and having a basis weight of about 60 gsy, available from Dupont Chemical Corp.

Alternatively, the water insoluble substrate can be a polymeric mesh sponge as described in European Patent No. EP 702550 A1 published Mar. 27, 1996, incorporated by reference herein in its entirety. The polymeric sponge comprises a plurality of plies of an extruded tubular netting mesh prepared from a strong flexible polymer, such as addition polymers of olefin monomers and polyamides of polycarboxylic acids. Although these polymeric sponges are designed to be used in conjunction with a liquid cleanser, these types of sponges can be used as the water insoluble substrate in the present invention.

The substrate can be made into a wide variety of shapes and forms including flat pads, thick pads, thin sheets, ball-shaped implements, irregularly shaped implements, and having sizes ranging from a surface area of about a square inch to about hundreds of square inches. The exact size will depend upon the desired use and product characteristics. Especially convenient are square, circular, rectangular, or oval pads having a surface area of from about 1 in$^2$ to about 144 in$^2$, preferably from about 10 in$^2$ to about 120 in$^2$, and more preferably from about 30 in$^2$ to about 80 in$^2$, and a thickness of from about 1 mil to about 500 mil, preferably from about 5 mil to about 250 mil, and more preferably from about 10 mil to about 100 mil.

The water insoluble substrates of the present invention can comprise two or more layers, each having different textures and abrasiveness. The differing textures can result from the use of different combinations of materials or from the use of different manufacturing processes or a combination thereof. A dual textured substrate can be made to provide the advantage of having a more abrasive side for exfoliation and a softer, absorbent side for gentle cleansing. In addition, separate layers of the substrate can be manufactured to have different colors, thereby helping the user to further distinguish the surfaces.

Active Protein

An essential component of the present invention is a plurality of active proteins. The active proteins are present on the surface of the water insoluble substrate at a level ranging from about 0.01 µg/cm$^2$ to about 1000 µg/cm$^2$, preferably from about 0.05 µg/cm$^2$ to about 100 µg/cm$^2$, and most preferably from about 0.1 µg/cm$^2$ to about 10 µg/cm$^2$.

An active protein is any amino acid based compound that is capable of inducing a human immune response due to exposure to the compound. The active protein will exhibit either biological function, catalytic activity or cosmetic utility or any combination thereof. Nonlimiting examples of active proteins are antibodies, antibody pieces, animal and vegetable proteins such as collagen, and soy, whey or wheat proteins, modified animal or vegetable proteins such as Crotein Q® (stearyl trimonium hydroxyethyl hydrolyzed collagen), and enzymes.

Any active protein can be used in the personal care wipe compositions of the present invention. Preferred active proteins are enzymes. Enzymes for use in the personal care wipe of the present invention may have any activity known to be used for skin care. These include but are not limited to oxidoreductases, such as laccase and superoxide dismutases; Hydrolases, including proteases and lipases; trasnferases such as transglutaminases and isomerases such as protein disulfide isomerases. Preferred enzymes are selected from the group consisting of lipase and protease enzymes, and mixtures thereof.

Lipase enzymes are classified under the Enzyme Classification number E.C. 3.1.1 (Carboxylic Ester Hydrolases) in accordance with the Recommendations (1992) of the International Union of Biochemistry and Molecular Biology (IUBMB). Examples of lipases include lipases derived from the following microorganisms. The indicated patent publications are incorporated herein by reference:

Humicola, (U.S. 4,810,414)

Pseudonomas (WO 89/04361, U.S. Pat. No. 4,950,417, EP 218 272, WO 88/09367, U.S. Pat. No. 5,389,536)

Fusarium (EP 130 064, WO 90/09446)

Mucor (EP 238 023)

Chromobacterium

Aspergillus

Candida (WO 88/02775, WO 94/01541, WO 89/02916)

Geotricum

Penicillium

Rhizopus

Bacillus (WO 91/16422)

Specific examples of commercial lipases include Lipolase®, Lipolase™ Ultra, Lipozyme®, Palatase®, Novozym435, Lecitase® (all available from Novo Nordisk A/S); Lumafast™ and Lipomax (available from Genencor Int., Inc.).

Protease enzymes are classified under the Enzyme Classification number E.C. 3.4 (Carboxylic Ester Hydrolases) in accordance with the Recommendations (1992) of the International Union of Biochemistry and Molecular Biology (IUBMB). Useful proteases are also described in PCT publications: WO 95/30010 published Nov. 9, 1995 by The Procter & Gamble Company; WO 95/30011 published Nov. 9, 1995 by The Procter & Gamble Company; WO 95/29979 published November 9, 1995 by The Procter & Gamble Company. Preferred protease enzymes for use in the personal care wipes herein are *subtilisin*, chymotrypsin and elastase-type protease enzymes.

Especially preferred for use herein are *subtilisin*-type protease enzymes. *Subtilisin* enzymes are naturally produced by *Bacillus alcalophilus, Bacillus amyloliquefaciens, Bacillus amylosaccharicus, Bacillus licheniformis, Bacillus lentus* and *Bacillus subtilis* microorganisms.

A particularly preferred *substilisin*-type enzyme is bacterial serine protease enzyme, and variants thereof, obtained from *Bacillus amyloliquefaciens, Bacillus licheniformis* and/or *Bacillus subtilis*, including Novo Industries A/S Alcalase®, Esperase®, Savinase® (Copenhagen, Denmark), Gist-brocades' Maxatase®, Maxacal® and Maxapem 15® (protein engineered Maxacal®) (Delft, Netherlands), and *subtilisin* BPN and BPN', which are commercially available.

Especially preferred are protease enzymes, and variants thereof, obtained from *Bacillus amyloliquefaciens*. One known enzyme is BPN'. The wild-type BPN' from *Bacillus amyloliquefaciens* is characterized by the amino acid sequence:

```
       1                              10                              20
Ala Gln Ser Val Pro Tyr Gly Val Ser Gln Ile Lys Ala Pro Ala Leu His Ser Gln Gly 30                              40
        Tyr Thr Gly Ser Asn Val Lys Val Ala Val Ile Asp Ser Gly Ile Asp Ser Ser His Pro 50                              60
        Asp Leu Lys Val Ala Gly Gly Ala Ser Met Val Pro Ser Glu Thr Asn Pro Phe Gln Asp 70                              80
```

-continued

```
Asn Asn Ser His Gly Thr His Val Ala Gly Thr Val Ala Ala Leu Asn Asn Ser Ile Gly
                                     90                                      100
Val Leu Gly Val Ala Pro Ser Ala Ser Leu Tyr Ala Val Lys Val Leu Gly Ala Asp Gly
                                    110                                      120
Ser Gly Gln Tyr Ser Trp Ile Ile Asn Gly Ile Glu Trp Ala Ile Ala Asn Asn Met Asp
                                    130                                      140
Val Ile Asn Met Ser Leu Gly Gly Pro Ser Gly Ser Ala Ala Leu Lys Ala Ala Val Asp
                                    150                                      160
Lys Ala Val Ala Ser Gly Val Val Val Val Ala Ala Ala Gly Asn Glu Gly Thr Ser Gly
                                    170                                      180
Ser Ser Ser Thr Val Gly Tyr Pro Gly Lys Tyr Pro Ser Val Ile Ala Val Gly Ala Val
                                    190                                      200
Asp Ser Ser Asn Gln Arg Ala Ser Phe Ser Ser Val Gly Pro Glu Leu Asp Val Met Ala
                                    210                                      220
Pro Gly Val Ser Ile Gln Ser Thr Leu Pro Gly Asn Lys Tyr Gly Ala Tyr Asn Gly Thr
                                    230                                      240
Ser Met Ala Ser Pro His Val Ala Gly Ala Ala Ala Leu Ile Leu Ser Lys His Pro Asn
                                    250                                      260
Trp Thr Asn Thr Gln Val Arg Ser Ser Leu Glu Asn Thr Thr Thr Lys Leu Gly Asp Ser
                                    270            275
Phe Tyr Tyr Gly Lys Lys Gly Leu Ile Asn Asn Val Gln Ala Ala Ala Gln
```

Variants of BPN' are also useful in the personal care wipe of the present invention. Several related variants, all hereafter referred to as "Protease A", are disclosed in U.S. Pat. No. 5,030,378 (issued to Venegas, Jul. 9, 1991) as characterized by the BPN' amino acid sequence with the following mutations:

a.) the Gly at position Gly166 is replaced with Asn, Ser, Lys, Arg, His, Gln, Ala or Glu; the Gly at position Gly169 is replaced with Ser; the Met at position Met222 is replaced with Gln, Phe, Cys, His, Asn, Glu, Ala or Thr; or b.) the Gly at position Gly166 is replaced with Lys and the Met at position Met222 is replaced with Cys; or c.) the Gly at position Gly160 is replaced with Ala and the Met at position Met222 is replaced with Ala.

Additional variants of BPN', heretoforth referred to as "Protease B", are disclosed by Genencor International, Inc. (San Francisco, Calif.) European Patent EP-B-251,446 (granted Dec. 28, 1994 and published Jan. 7, 1988) as characterized by the wild-type BPN' amino acid with the mutations in one or more of the following amino acids: Tyr21, Thr22, Ser24, Asp36, Ala45, Ala48, Ser49, Met50, His67, Ser87, Lys94, Val95, Gly97, Ser101, Gly102, Gly103, Ile107, Gly110, Met124, Gly127, Gly128, Pro129, Leu135, Lys170, Tyr171, Pro172, Asp197, Met199, Ser204, Lys213, Tyr214, Gly215, and Ser221; or two or more of the amino acids listed above and Asp32, Ser33, Tyr104, Ala152, Asn155, Glu156, Gly166, Gly169, Phe189, Tyr217, and Met222 wherein both mutations cannot be made on the Asp32, Ser33, Tyr104, Ala152, Asn155, Glu156, Gly166, Gly169, Phe189, Tyr217, and Met222 amino acids.

Another preferred BPN' variant protease, hereafter referred to as "Protease D", is described in WO 95/10615 published Apr. 20, 1995 by Genencor International as characterized by the wild-type BPN' amino acid with mutation to position Asn76, in combination with mutations in one or more other amino acid positions selected from the group consisting of Asp99, Ser101, Gln103, Tyr104, Ser105, Ile107, Asn109, Asn123, Leu126, Gly127, Gly128, Leu135, Glu156, Gly166, Glu195, Asp197, Ser204, Gln206, Pro210, Ala216, Tyr217, Asn218, Met222, Ser260, Lys265, and/or Ala274.

Another preferred BPN' variant protease, hereafter referred to as "Protease F", is described in U.S. Pat. No. 4,760,025, issued to Estell, et al. on Jul. 26, 1988 as characterized by the wild-type BPN' amino acid with mutation to one or more amino acid positions selected from the group consisting of Asp32, Ser33, His64, Tyr104, Asn155, Glu156, Gly166, Gly169, Phe189, Tyr217, and Met222.

Preferred proteolytic enzymes, then, are selected from the group consisting of Alcalase®, BPN', Protease A, Protease B, Protease D, Protease F, and mixtures thereof.

An additional class of active proteins are "singularly substituted proteins", those proteins wherein the parent amino acid sequence is substituted at one of the amino acid residues with a substitute amino acid which is not present elsewhere in the parent amino acid. Singularly substituted proteins also encompass those proteins wherein one amino acid which is not present in the parent amino acid is inserted into the amino acid sequence. The substituted or inserted amino acid provides a moiety suitable for attachment to the substrate of the present invention at a specific site within the protein.

Preferably the substitution or insertion should be made at a position in an epitope region which falls at a point in the protein away from the active site of the protein. One embodiment of these singularly substituted proteins, hereinafter referred to as Protease G, is a modification of *subtilisin* BPN' and its derivatives. The active site in *subtilisin* BPN' type enzymes is defined by the spacial triad of Asn32, His64, and Ser 221. In a Protease G enzyme, a cysteine is substituted or inserted at a point away from that triad. Preferable epitope regions for substitution are the of Asp140-Val150 and Ala230-Leu250 region. Non-limiting examples of possible cysteine substitutions at either Ser145, Asn 240 or Ser249. Cysteine is the most preferred substituting amino acid for substitution in the desired epitope region since it does not occur in wild-type *subtilisin* BPN' or its derivatives.

Binding Means

The active proteins are bound to the water insoluble substrate by any suitable binding means which comprises a polymeric tether. Binding means include any chemical method of permanently binding an active protein to a substrate.

Protein Tethered to Polymeric Gel Coating on Substrate

The protein may be bound to the substrate by a polymeric tether bound to a polymeric coating on the substrate. The protein is bonded to a polymeric tether which is covalently attached to the polymer coating. One embodiment is the use of polyethylene glycol (PEG)-N-hydroxy succinimide as the polymeric tether bound to an poly-2-hydroxyethyl acrylate coating.

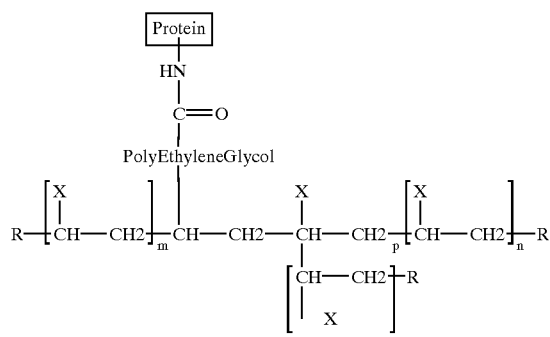

Another embodiment of a polymeric tether is Polyethylene glycol (PEG)-Maleimide, sold by Shearwater Polymers, Inc. PEG-Maleimide must be used with a cysteine amino acid, therefore it may be used when the active protein is Protease G. PEG-Maleimide may also be used in conjunction with a poly-2-hydroxyethyl acrylate coating. A generic structure of a preferred acrylate-PEG-Maleimide tether can be represented by the formula:

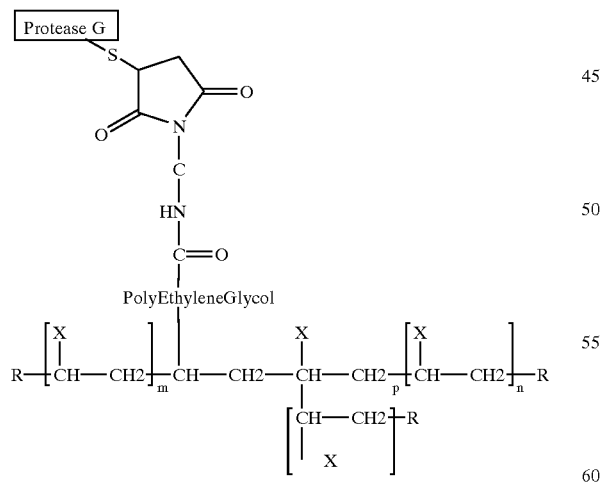

Yet another embodiment of a cysteine containing protein tethered to a polymeric coating on the wipe substrate comprises a PEG-Maleimid covalently bonded to a polyethyleneimine coating by N-hydroxysuccinimdie (NHS) as represented by the formula:

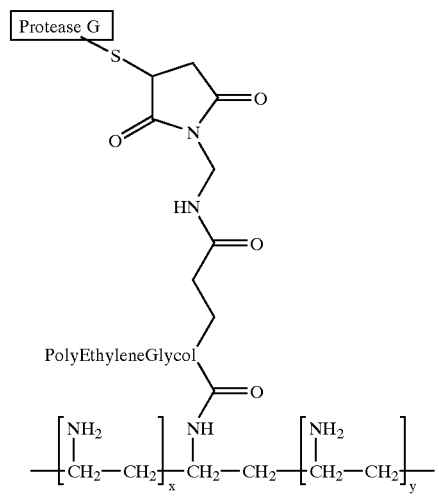

Binding means comprising tethered proteins are preferred over physical entrapment and direct covalent attachment since tethered proteins are more mobile and are less covered by the polymer coating, both of which provide more activity of the proteins.

Protein Covalently Linked to Activated Implement Surface Via Polymeric Tether Yet another means for binding the active protein to the substrate of the personal care wipe of the present invention is a polymeric tether covalently bonded to an activated site on the surface of the substrate. The preferred tether is ethylenediamine/polyethylene glycol-Maleimide. A generic structure of a directly bonded ethylenediamine/PEG-Maleimide tether can be represented by the formula:

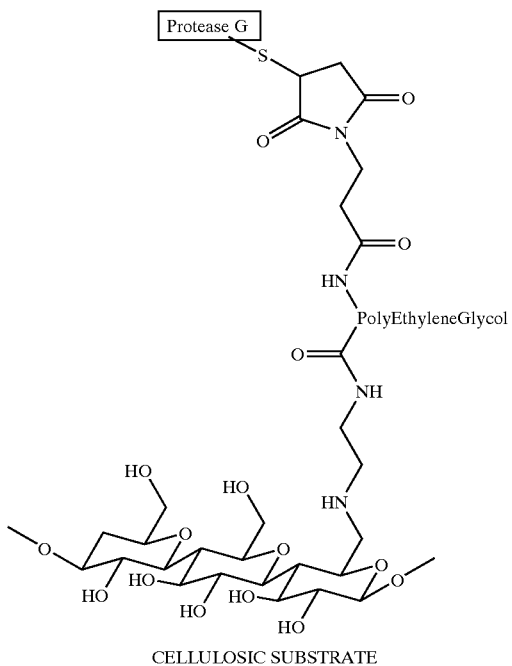

CELLULOSIC SUBSTRATE

Optional Ingredients

The wipe compositions of the present invention can comprise a wide range of optional ingredients. The *CTFA International Cosmetic Ingredient Dictionary*, Sixth Edition, 1995, which is incorporated by reference herein in its entirety, describes a wide variety of nonlimiting cosmetic and pharmaceutical ingredients commonly used in the skin care industry, which are suitable for use in the compositions of the present invention. Nonlimiting examples of functional classes of ingredients are described at page 537 of this reference. Examples of these functional classes include: abrasives, anti-acne agents, anticaking agents, antimicrobial agents, antioxidants, binders, biological additives, bulking agents, chelating agents, chemical additives, colorants, cosmetic astringents, cosmetic biocides, denaturants, drug astringents, emulsifiers, external analgesics, film formers, fragrance components, humectants, mildness enhancers (cationic and nonionic polymers, co-surfactants, lipid moisturizers, hydrocarbon oils, silicone oils, waxes), opacifying agents, plasticizers, preservatives, propellants, reducing agents, skin bleaching agents, skin-conditioning agents (emollient, humectants, miscellaneous, and occlusive), skin protectants, solvents, foam boosters, hydrotropes, solubilizing agents, stabilizers, suspending agents, sunscreen agents, surfactants (anionic, cationic, amphoteric, zwitterionic), ultraviolet light absorbers, and viscosity increasing agents (aqueous and nonaqueous). Examples of other functional classes of materials useful herein that are well known to one of ordinary skill in the art include solubilizing agents, sequestrants, and keratolytics, and the like.

Methods of Use

The personal care compositions of the present invention are useful for personal cleansing, cosmetic skin treatment, and/or skin conditioning. The present invention may take the form of a personal care wipe or a personal care skin mask. Typically, the wipe is used to expose the area to be cleansed to the active enzymes for a relatively short period of time. For use, the wipe is contacted with or wiped skin which needs treatment and then removed. Typical quantities of the present wipes useful for cleansing, range from about 1 to about 4 wipes per use, preferably from about 1 to about 2 wipes per use. The skin mask is used to expose the area to be treated for a relatively longer period of time. Typical quantities of the present skin masks useful for cleansing, range from about 1 to about 2 masks per use, preferably 1 mask per use.

EXAMPLES AND METHODS OF MANUFACTURE

The following examples further describe and demonstrate embodiments within the scope of the present invention. In the following examples, all ingredients are listed at an active level. The examples are given solely for the purpose of illustration and are not to be construed as limitations of the present invention, as many variations thereof are possible without departing from the spirit and scope of the invention. Ingredients are identified by chemical or CTFA name.

The following are nonlimiting examples of the wipes with bound active proteins of the present invention.

Example 1

Protease F Tethered to Polymeric Coating

Purify and concentrate Protease F to approximately 2.5 mg/mL in 10 mM $KH_2PO_4$ buffer, pH 5.5. Add Acrylate-$PEG_{3400}$-N-hydroxysuccinimide (Shearwater Polymers, Inc.) in a 15:1 molar excess. Raise the solution pH to 7 with dilute sodium hydroxide (NaOH). Let Protease F and Acrylate-PEG-N-hydroxysuccinimide react for 1–2 hours at room temperature. Drop the solution pH to 5.5 with dilute phosphoric acid ($H_3PO_4$). Add 2-hydroxyethyl acrylate (HEA) to the Protease F-PEG-N-hydroxysuccinimide solution to achieve a final molar concentration of 1.3 M. Add 50 mM $H_2O_2$ solution to the Protease F-PEG/HEA solution such that a final molar concentration of 2.5 mM $H_2O_2$ exists. Spray the solution onto a rayon/PET sheet until the sheet has become saturated. Separately spray 50 mM iron (II) sulfate heptahydrate ($FeSO_4.7H_2O$) solution onto the sheet such that the entire surface area is sprayed uniformly. Allow the sheet to sit for 5 minutes. Then rinse the sheet through successive 0.01M $KH_2PO_4$ baths until all free Protease F has been removed. Dry sheets.

Example 2

Protease G tethered to Polymeric Coating

Purify and concentrate Protease G to approximately 2.5 mg/mL in 10 mM $KH_2PO_4$ buffer, pH 5.5. Add Acrylate-$PEG_{3400}$-Maleiminde (Shearwater Polymers, Inc.) in a 15:1 molar excess. Raise the solution pH to 7 with dilute sodium hydroxide (NaOH). Let Protease G and Acrylate-PEG-Maleimide react for 1–2 hours at room temperature. Drop the solution pH to 5.5 with dilute phosphoric acid ($H_3PO_4$). Add 2-hydroxyethyl acrylate (HEA) to the Protease G-PEG-Maleimide solution to achieve a final molar concentration of 1.3 M. Add 50 mM $H_2O_2$ solution to the Protease G-PEG/HEA solution such that a final molar concentration of 2.5 mM $H_2O_2$ exists. Spray the solution onto a rayon/PET sheet until the sheet has become saturated. Separately spray 50 mM iron (II) sulfate heptahydrate ($FeSO_4.7H_2O$) solution onto the sheet such that the entire surface area is sprayed uniformly. Allow the sheet to sit for 5 minutes. Then rinse the sheet through successive 0.01M $KH_2PO_4$ baths until all free Protease G has been removed. Dry sheets.

Example 3

Protease G Covalently Linked to Activated Implement Surface via Polymer Tether

Soak rayon/PET sheets in an aqueous 10% (w/v) NaOH solution for 10–15 minutes with shaking on auto-shaker, using 1 mL solution per 1 $cm^2$ sheet. Wash sheets three times with deionized water under suction (~1 ml/$cm^2$/wash). Wash sheets five times with acetone under suction. Allow sheets to soak in acetone for 1 minute between washes. React sheets in a 10% (w/v) p-toluenesulfonyl chloride in acetone solution for 25–30 minutes with shaking (~1 ml/$cm^2$). Rinse sheets 3 times with acetone under suction to remove excess p-toluenesulfonyl chloride. React sheets in 2.2M ethylenediamine in acetone solution, pH 13–14, for 2 hours with shaking. Rinse sheets 3 times with acetone under suction to remove excess EDA. Rinse sheets 5 times with 0.2M sodium borate buffer, pH 8.5 under suction. Let sheets soak for 1 minute in buffer between rinses. React sheets in 3–5% (w/v) Maliemide-$PEG_{3400}$-NHS (Shearwater Polymers, Inc.) in 0.2M sodium borate buffer, pH 8.5 for 1–2 hours with shaking (~1 ml/$cm^2$). Rinse sheets 5 times with 10 mM $KH_2PO_4$ buffer, pH 7, under suction to remove excess PEG. React sheets in 3 mg/ml Protease G in 10 mM $KH_2PO_4$ buffer, pH 7 (~1 ml/$cm^2$) for approximately 1–2 hours. Rinse sheets 3 times with 0.01M $KH_2PO_4$ buffer, pH 5.5. Dry sheets.

Example 4

Protease a Covalently Linked to Activated Implement Surface via Polymer Tether

Soak rayon/PET sheets in an aqueous 10% (w/v) NaOH solution for 10–15 minutes with shaking on auto-shaker, using 1 mL solution per 1 cm² sheet. Wash sheets three times with deionized water under suction (~1 ml/cm²/wash). Wash sheets five times with acetone under suction. Allow sheets to soak in acetone for 1 minute between washes. React sheets in a 10% (w/v) p-toluenesulfonyl chloride in acetone solution for 25–30 minutes with shaking (~1 ml/cm²). Rinse sheets 3 times with acetone under suction to remove excess p-toluenesulfonyl chloride. React sheets in 2.2M ethylenediamine in acetone solution, pH 13–14, for 2 hours with shaking. Rinse sheets 3 times with acetone under suction to remove excess EDA. Rinse sheets 5 times with 0.2M sodium borate buffer, pH 8.5 under suction. Let sheets soak for 1 minute in buffer between rinses. React sheets in 3–5% (w/v) N-hydroxysuccinimide-PEG$_{3400}$-NHS (Shearwater Polymers, Inc.) in 0.2M sodium borate buffer, pH 8.5 for 1–2 hours with shaking (~1 ml/cm²). Rinse sheets 5 times with 10 mM KH$_2$PO$_4$ buffer, pH 7, under suction to remove excess PEG. React sheets in 3 mg/ml Protease A in 10 mM KH$_2$PO$_4$ buffer, pH 7 (~1 ml/cm²) for approximately 1–2 hours. Rinse sheets 3 times with 0.01M KH$_2$PO$_4$ buffer, pH 5.5. Dry sheets.

Example 5

Protease G Covalently Linked to Coated Implement Surface via Polymer Tether

Soak rayon/PET sheets in 500 ppm bath of polyethyleneimine for 1 hour with shaking at room temperature (~1–2 ml/cm² sheet). Rinse rayon/PET sheets in 2 successive 0.2M sodium borate buffer, pH 12, baths (~5–10 ml/cm²). Rinse sheets in 2 successive 0.2M sodium borate buffer, pH 8.5, baths. React sheets in 5 mg/mL NHS-PEG$_{3400}$-Maleimide in 0.2M sodium borate buffer, pH 8.5, with shaking at room temperature for 1 hour. Rinse cloths through 4 deionized water baths (~5–10 ml/cm²). Rinse cloths through 2 0.01M KH$_2$PO$_4$ buffer, pH 7–7.5, baths. Separately, purify and concentrate Protease G to 1–2 mg/ml in 0.01M KH$_2$PO$_4$ buffer, pH 7–7.5. React "PEGylated" sheets in Protease G solution, pH 7–7.5, for 1 hour at room temperature with shaking. Rinse sheets through 5 successive 0.01M KH$_2$PO$_4$, pH 5.5, baths to remove unreacted, unbound Protease G. Let sheets dry.

Examples 6–9

A personal care wipe composition product is prepared as follows:

|  | Weight Percent | | | |
| --- | --- | --- | --- | --- |
| Ingredients | Example 6 | Example 7 | Example 8 | Example 9 |
| Phase A | | | | |
| Water | QS 100 | QS 100 | QS 100 | QS 100 |
| Glycerin | 10.00 | 10.00 | 10.00 | 10.00 |
| Disodium Lauroamphodiacetate (and) Sodium Trideceth Sulfate | 4.00 | 4.00 | — | — |
| Sodium Lauroamphoacetate | — | — | 2.40 | 2.40 |
| Sodium Lauroyl Sarcosinate | 4.00 | 4.00 | — | — |
| Ammonium Laureth Sulfate | — | — | 4.20 | 4.20 |
| Ammonium Lauryl Sulfate | — | — | 1.40 | 1.40 |
| Polyquarternium-10 | 0.25 | 0.25 | 0.25 | 0.25 |
| Disodium EDTA | 0.10 | 0.10 | 0.10 | 0.10 |
| Phase B | | | | |
| Sucrose Ester Fatty Acid Cottonate | 3.00 | 3.00 | 3.00 | 3.00 |
| Petrolatum | — | 1.50 | — | — |
| Cetyl Dimethicone | — | — | — | 2.00 |
| Phase C | | | | |
| Butylene Glycol | 2.00 | 2.00 | 2.00 | 2.00 |
| DMDM Hydantoin (and) Iodopropynyl Carbamate | 0.20 | 0.20 | 0.20 | 0.20 |

Water Insoluble Substrate

A hydroapertured, nonwoven substrate having a basis weight of about 60 gsy comprising 50% rayon and 50% polyester approximately 6 in. by 7.6 in. and a thickness of about 20 mil having a bound active protein per Examples 1–5.

In a suitable vessel., the Phase A ingredients are mixed at room temperature to form a dispersion and heated with stirring to 65° C. The Phase B ingredients are mixed in a separate suitable vessel and heated to 65° C. Once the temperatures are the same, the Phase B ingredients are mixed into the vessel containing the Phase A ingredients and then cooled to 45° C. The Phase C ingredients are then mixed together in a separate vessel at room temperature. Next, the Phase C mixture is added into the vessel containing the combination of Phases A and B at room temperature. 1.5 grams of the resulting solution is sprayed onto each substrate. Alternatively, the substrate can be dipped into the resulting solution. The treated substrate is then dried in an oven to constant weight. Alternatively, the treated substrate is dried in a convection oven at 45° C. to constant weight.

In alternative embodiments, other substrates such as woven substrates, hydroentangled substrates, natural sponges, synthetic sponges, or polymeric netted meshes. Alternative embodiments may be in the from of person care skin masks.

Examples 10–13

A personal care wipe is prepared as follows:

|  | Weight Percent | | | |
| --- | --- | --- | --- | --- |
| Ingredients | Example 10 | Example 11 | Example 12 | Example 13 |
| Phase A | | | | |
| Water | QS 100 | QS 100 | QS 100 | QS 100 |
| Glycerin | 10.00 | 10.00 | 10.00 | 10.00 |
| Panthenol | 0.50 | — | 0.50 | 0.50 |
| Sodium Lauroamphoacetate | 2.40 | 2.40 | 2.40 | 2.40 |
| Ammonium Lauryl Sulfate | 1.40 | 1.40 | 1.40 | 1.40 |
| Polyquarternium-10 | 0.25 | 0.25 | 0.25 | 0.25 |
| Disodium EDTA | 0.10 | 0.10 | 0.10 | 0.10 |
| Phase B | | | | |
| Sucrose Ester Fatty Acid Cottonate | 3.00 | 3.00 | 3.00 | 3.00 |
| Petrolatum | — | — | — | 0.50 |
| Cetyl Dimethicone | — | — | — | 0.50 |
| Cetyl Ricinoleate | — | 2.00 | 2.00 | 1.00 |

-continued

| Ingredients | Weight Percent | | | |
|---|---|---|---|---|
| | Example 10 | Example 11 | Example 12 | Example 13 |
| Phase C | | | | |
| Butylene Glycol | 2.00 | 2.00 | 2.00 | 2.00 |
| DMDM Hydantoin (and) Iodopropynyl Carbamate | 0.20 | 0.20 | 0.20 | 0.20 |

Water Insoluble Substrate

A hydroapertured, nonwoven substrate having a basis weight of about 60 gsy comprising 50% rayon and 50% polyester approximately 6 in. by 7.6 in. and a thickness of about 20 mil having a bound active protein per Examples 1–5.

In a suitable vessel., the Phase A ingredients are mixed at room temperature to form a dispersion and heated with stirring to 65° C. The Phase B ingredients are mixed in a separate suitable vessel and heated to 65° C. Once the temperatures are the same, the Phase B ingredients are mixed into the vessel containing the Phase A ingredients and then cooled to 45° C. Next, the Phase C mixture is added into the vessel containing the combination of Phases A and B at room temperature. 1.5 grams of the resulting solution is sprayed onto each substrate. Alternatively, the substrate can be dipped into the resulting solution. The treated substrate is then dried in an oven to constant weight. Alternatively, the treated substrate is dried in a convection oven at 45° C. to constant weight.

In alternative embodiments, other substrates such as woven substrates, hydroentangled substrates, natural sponges, synthetic sponges, or polymeric netted meshes. Alternative embodiments may be in the from of person care skin masks.

Examples 14–17

| Ingredients | Weight Percent | | | |
|---|---|---|---|---|
| | Example 14 | Example 15 | Example 16 | Example 17 |
| Phase A | | | | |
| Water | QS 100 | QS 100 | QS 100 | QS 100 |
| Disodium Lauroamphodiacetate (and) Sodium Trideceth Sulfate | 4.00 | 4.00 | — | — |
| Sodium Lauroamphoacetate | — | — | 2.40 | 2.40 |
| Sodium Lauroyl Sarcosinate | 4.00 | 4.00 | — | — |
| Ammonium Laureth Sulfate | — | — | 4.20 | 4.20 |
| Ammonium Lauryl Sulfate | — | — | 1.40 | 1.40 |
| Disodium EDTA | 0.10 | 0.10 | 0.10 | 0.10 |
| Phase B | | | | |
| Sucrose Ester Fatty Acid Cottonate | 3.00 | 3.00 | 3.00 | 3.00 |
| Petrolatum | — | 1.50 | — | — |
| Cetyl Dimethicone | — | — | — | 2.00 |
| Phase C | | | | |
| DMDM Hydantoin (and) Iodopropynyl Carbamate | 0.20 | 0.20 | 0.20 | 0.20 |

Water Insoluble Substrate

A hydroapertured, nonwoven substrate having a basis weight of about 60 gsy comprising 50% rayon and 50% polyester approximately 6 in. by 7.6 in. and a thickness of about 20 mil having a bound active protein per Examples 1–5.

In a suitable vessel., the Phase A ingredients are mixed at room temperature to form a dispersion and heated with stirring to 65° C. The Phase B ingredients are mixed in a separate suitable vessel and heated to 65° C. Once the temperatures are the same, the Phase B ingredients are mixed into the vessel containing the Phase A ingredients and then cooled to 45° C. The Phase C ingredients are then mixed together in a separate vessel at room temperature. Next, the Phase C mixture is added into the vessel containing the combination of Phases A and B at room temperature. 1.5 grams of the resulting solution is sprayed each substrate. Alternatively, the substrate can be dipped into the solution. The treated substrate is then dried in an oven to constant weight. Alternatively, the treated substrate is dried in a convection oven at about 45° C. to constant weight.

In alternative embodiments, other substrates such as woven substrates, hydroentangled substrates, natural sponges, synthetic sponges, or polymeric netted meshes. Alternative embodiments may be in the from of person care skin masks.

Examples 18–21

| Ingredients | Weight Percent | | | |
|---|---|---|---|---|
| | Example 18 | Example 19 | Example 20 | Example 21 |
| Phase A | | | | |
| Water | QS 100 | QS 100 | QS 100 | QS 100 |
| Sodium Lauroamphoacetate | 2.40 | 2.40 | 2.40 | 2.40 |
| Ammonium Laureth Sulfate | 4.20 | 4.20 | 4.20 | 4.20 |
| Ammonium Lauryl Sulfate | 1.40 | 1.40 | 1.40 | 1.40 |
| Disodium EDTA | 0.10 | 0.10 | 0.10 | 0.10 |
| Phase B | | | | |
| Sucrose Ester Fatty Acid Cottonate | 3.00 | 3.00 | 3.00 | 3.00 |
| Petrolatum | — | 0.50 | 1.00 | — |
| Cetyl Dimethicone | — | 0.50 | — | 1.00 |
| Cetyl Ricinoleate | 2.00 | 0.50 | 1.00 | 1.00 |
| Phase C | | | | |
| DMDM Hydantoin (and) Iodopropynyl Carbamate | 0.20 | 0.20 | 0.20 | 0.20 |

Water Insoluble Substrate

A hydroapertured, nonwoven substrate having a basis weight of about 60 gsy comprising 50% rayon and 50% polyester approximately 6 in. by 7.6 in. and a thickness of about 20 mil having a bound active protein according to Examples 1–5.

In a suitable vessel., the Phase A ingredients are mixed at room temperature to form a dispersion and heated with stirring to 65° C. The Phase B ingredients are mixed in a separate suitable vessel and heated to 65° C. Once the temperatures are the same, the Phase B ingredients are mixed into the vessel containing the Phase A ingredients and then cooled to 45° C. Next, the Phase C mixture is added into the vessel containing the combination of Phases A and B at room temperature. 1.5 grams of the resulting solution is sprayed onto each substrate. Alternatively, the substrate can be dipped into the solution. The treated substrate is then dried in an oven to constant weight. Alternatively, the treated substrate is dried in a convection oven at about 45° C. to constant weight.

In alternative embodiments, other substrates such as woven substrates, hydroentangled substrates, natural sponges, synthetic sponges, or polymeric netted meshes. Alternative embodiments may be in the from of person care skin masks.

What is claimed:

1. A personal care wipe composition comprising:
   a) a water insoluble substrate,
   b) a plurality of active proteins, and
   c) a binding means, comprising a polymeric tether, permanently attaching each of the enzymes to the substrate;
   wherein the personal care wipe composition comprises from about 0.01 $\mu g/cm^2$ to about 1000 $\mu g/cm^2$ of the enzyme on the substrate.

2. A personal care wipe composition according to claim 1 wherein said water insoluble substrate comprises one or more materials selected from the group consisting of silks, keratins, celluloses, acetates, acrylics, cellulose esters, modacrylics, polyamides, polyesters, polyolefins, polyvinyl alcohols, wood pulp, cotton, hemp, jute, flax, acrylics, nylons, polyesters, polyproylenes, polyethylenes, polyvinyl acetates, polyurethanes, rayon, and mixtures thereof.

3. A personal care wipe composition according to claim 2 wherein said water insoluble substrate comprises a nonwoven sheet of fibers selected from the group consisting of rayon fibers, cellulose fibers, polyester fibers, and mixtures thereof.

4. A personal care wipe composition according to claim 3 wherein said water insoluble substrate comprises two or more sheets of fibers each in turn having different textures.

5. A personal care wipe composition according to claim 1 wherein the active proteins are enzymes selected from the group consisting of protease enzymes, lipase, enzymes, and mixtures thereof.

6. A personal care wipe composition according to claim 5, wherein the enzyme is selected from the group consisting of *subtilisin,* chymotrypsin, and elastase-type enzymes, and mixtures thereof.

7. A personal care wipe composition according to claim 6, wherein the enzyme is selected from the group consisting of Alcalase®, BPN', Protease A, Protease B, Protease D, Protease F, and mixtures thereof.

8. A personal care wipe composition according to claim 6, wherein the enzyme is a singularly substituted protein.

9. A personal care wipe composition according to claim 8, wherein the singularly substituted protein is substituted at a point spacially away from the active site of the protein.

10. A personal care wipe composition according to claim 9, wherein the singularly substituted protein is Protease G.

11. A personal care wipe composition according to claim 1, wherein the polymeric tether comprises polyethylene glycol-maleimide.

12. A personal care wipe composition according to claim 1, wherein the polymeric tether comprises polyethylene glycol-N-hydroxysuccinimide.

13. A personal care wipe composition according to claim 1, wherein the binding means comprises a polymeric tether and a polymeric coating.

14. A personal care wipe composition according to claim 13 wherein the polymeric tether comprises polyethylene glycol-maleimide and the polymeric coating comprises poly-2-hydroxyethyl acrylate.

15. A personal care wipe composition according to claim 13, wherein the polymeric tether comprises polyethylene glycol-maleimide and the polymeric coating comprises polyethyleneimine.

16. A personal care wipe composition according to claim 13, wherein the polymeric tether comprises polyethylene glycol-N-hydroxysuccinimide and the polymeric coating comprises poly-2-hydroxyethyl acrylate.

17. A personal care wipe composition according to claim 13, wherein the polymeric tether comprises polyethylene glycol-N-hydroxysuccinimide and the polymeric coating comprises polyethyleneimine.

18. A personal care wipe composition according to claim 10 wherein the polymeric tether comprises polyethylene glycol-maleimide and the polymeric coating comprises poly-2-hydroxyethyl acrylate.

19. A personal care wipe composition according to claim 10, wherein the polymeric tether comprises polyethylene glycol-maleimide and the polymeric coating comprises polyethyleneimine.

20. A personal care skin mask composition comprising:
    a) a water insoluble substrate,
    b) a plurality of active proteins, and
    c) a binding means, comprising a polymeric tether, permanently attaching each of the enzymes to the substrate;
    wherein the personal care wipe composition comprises from about 0.01 $\mu g/cm^2$ to about 1000 $\mu g/cm^2$ of the enzyme on the substrate.

21. A personal care skin mask composition according to claim 20 wherein said water insoluble substrate comprises one or more materials selected from the group consisting of silks, keratins, celluloses, acetates, acrylics, cellulose esters, modacrylics, polyamides, polyesters, polyolefins, polyvinyl alcohols, wood pulp, cotton, hemp, jute, flax, acrylics, nylons, polyesters, polyproylenes, polyethylenes, polyvinyl acetates, polyurethanes, rayon, and mixtures thereof.

22. A personal care skin mask composition according to claim 21 wherein said water insoluble substrate comprises a nonwoven sheet of fibers selected from the group consisting of rayon fibers, cellulose fibers, polyester fibers, and mixtures thereof.

23. A personal care skin mask composition according to claim 22 wherein said water insoluble substrate comprises two or more sheets of fibers each in turn having different textures.

24. A personal care skin mask composition according to claim 20 wherein the active proteins are enzymes selected from the group consisting of protease enzymes, lipase, enzymes, and mixtures thereof.

25. A personal care skin mask composition according to claim 24, wherein the enzyme is selected from the group consisting of *subtilisin,* chymotrypsin, and elastase-type enzymes, and mixtures thereof.

26. A personal care skin mask composition according to claim 25, wherein the enzyme is selected from the group consisting of Alcalase®, BPN', Protease A, Protease B, Protease D, Protease F, and mixtures thereof.

27. A personal care skin mask composition according to claim 25, wherein the enzyme is a singularly substituted protein.

28. A personal care skin mask composition according to claim 27, wherein the singularly substituted protein is substituted at a point spacially away from the active site of the protein.

29. A personal care skin mask composition according to claim 28, wherein the singularly substituted protein is Protease G.

30. A personal care skin mask composition according to claim 20, wherein the polymeric tether comprises polyethylene glycol-maleimide.

31. A personal care skin mask composition according to claim 20, wherein the polymeric tether comprises polyethylene glycol-N-hydroxysuccinimide.

32. A personal care skin mask composition according to claim 20, wherein the binding means comprises a polymeric tether and a polymeric coating.

33. A personal care skin mask composition according to claim 32 wherein the polymeric tether comprises polyethylene glycol-maleimide and the polymeric coating comprises poly-2-hydroxyethyl acrylate.

34. A personal care skin mask composition according to claim 32, wherein the polymeric tether comprises polyethylene glycol-maleimide and the polymeric coating comprises polyethyleneimine.

35. A personal care skin mask composition according to claim 32, wherein the polymeric tether comprises polyethylene glycol-N-hydroxysuccinimide and the polymeric coating comprises poly-2-hydroxyethyl acrylate.

36. A personal care skin mask composition according to claim 32, wherein the polymeric tether comprises polyethylene glycol-N-hydroxysuccinimide and the polymeric coating comprises polyethyleneimine.

37. A personal care skin mask composition according to claim 29 wherein the polymeric tether comprises polyethylene glycol-maleimide and the polymeric coating comprises poly-2-hydroxyethyl acrylate.

38. A personal care skin mask composition according to claim 29, wherein the polymeric tether comprises polyethylene glycol-maleimide and the polymeric coating comprises polyethyleneimine.

39. A method for improving skin condition comprising the contacting of the personal care wipe composition of claim 1 with skin in need of such treatment.

40. A method for improving skin condition comprising the contacting of the personal care wipe composition of claim 18 with skin in need of such treatment.

41. A method for improving skin condition comprising the contacting of the personal care wipe composition of claim 19 with skin in need of such treatment.

42. A method for improving skin condition comprising the contacting of the personal care skin mask composition of claim 20 with skin in need of such treatment.

43. A method for improving skin condition comprising the contacting of the personal care skin mask composition of claim 37 with skin in need of such treatment.

44. A method for improving skin condition comprising the contacting of the personal care skin mask composition of claim 38 with skin in need of such treatment.

* * * * *